(12) United States Patent
Rau et al.

(10) Patent No.: US 8,010,210 B2
(45) Date of Patent: Aug. 30, 2011

(54) APPARATUS AND SYSTEM FOR INSERTION OF AN IMPLANT

(75) Inventors: Thomas Stephan Rau, Hannover (DE); Andreas Hussong, Hannover (DE); Omid Majdani, Berlin (DE); Martin Leinung, Hannover (DE); Thomas Lenarz, Hannover (DE); Hubertus Eilers, Hannover (DE); Stephan Baron, Hannover (DE)

(73) Assignees: Medizinische Hochschule Hannover, Hannover (DE); Leibniz Universitat Hannover, Hannover (DE)

( * ) Notice: Subject to any disclaimer, the term of this patent is extended or adjusted under 35 U.S.C. 154(b) by 475 days.

(21) Appl. No.: 12/244,275

(22) Filed: Oct. 2, 2008

(65) Prior Publication Data

US 2009/0275818 A1    Nov. 5, 2009

(30) Foreign Application Priority Data

Apr. 30, 2008    (EP) .................................... 08103802

(51) Int. Cl.
*A61N 1/05*    (2006.01)
(52) U.S. Cl. ........................... 607/137; 606/129; 607/55
(58) Field of Classification Search .............. 607/55–57, 607/137; 606/104, 114, 129
See application file for complete search history.

(56) References Cited

U.S. PATENT DOCUMENTS

| | | | |
|---|---|---|---|
| 5,800,500 A | 9/1998 | Spelman | |
| 5,944,739 A * | 8/1999 | Zlock et al. | 606/232 |
| 5,999,859 A | 12/1999 | Jolly | |
| 6,102,926 A * | 8/2000 | Tartaglia et al. | 606/170 |
| 6,163,729 A | 12/2000 | Kuzma | |
| 6,374,143 B1 | 4/2002 | Berrang | |
| 6,408,855 B1 | 6/2002 | Berrang | |
| 7,063,708 B2 * | 6/2006 | Gibson et al. | 606/129 |
| 7,181,288 B1 * | 2/2007 | Rezai et al. | 607/116 |
| 7,269,461 B2 | 9/2007 | Dadd | |
| 7,792,586 B2 * | 9/2010 | Dadd et al. | 607/57 |
| 2005/0085715 A1 | 4/2005 | Dukeshereer et al. | |
| 2007/0043378 A1 * | 2/2007 | Kumar et al. | 606/104 |
| 2007/0225787 A1 | 9/2007 | Simaan et al. | |

FOREIGN PATENT DOCUMENTS

DE    10 2005 039 455 A1    3/2007
WO    WO 03/070133    8/2003

* cited by examiner

*Primary Examiner* — Carl H Layno
*Assistant Examiner* — Brian T Gedeon
(74) *Attorney, Agent, or Firm* — Greer, Burns & Crain Ltd.

(57) ABSTRACT

The present invention provides an apparatus for insertion of a flexible implant into a body section of an implant recipient, the apparatus comprising an elongate guiding section having a longitudinal axis and an inner volume for removably receiving the implant, an elongate first receiving member connected at its first end to a first actuator arranged for moving the first receiving member within the guiding section in parallel to the axis of the guiding section, a first control device for controlling the actuation of the first actuator, wherein first receiving member at its second end opposite its first end carries a gripping unit for releasably gripping a proximal end of the implant, a second actuator for controlling the configuration of the implant, and a second control device for controlling the actuation of the second actuator.

25 Claims, 3 Drawing Sheets

APPARATUS AND SYSTEM FOR INSERTION OF AN IMPLANT

PRIORITY CLAIM

Priority of application Ser. No. 8,103,802 filed on Apr. 30, 2008 in the EP is claimed under 35 U.S.C. §119.

The present invention relates to an apparatus for insertion of an implant, preferably of a bio-compatible or bio-inert, e.g. synthetic implant like a device for delivery of electric stimuli to tissue, also referred to as an electrically stimulating implant, e.g. a cochlea implant having electrode surfaces for emitting electric stimuli. The implant is intended for implantation into the body or a body cavity of an implant recipient, and the invention provides an apparatus for insertion and a system comprising the apparatus and a control unit disposed to control the actuation of the apparatus during insertion of the implant. The apparatus for insertion is disposed for control of the insertion process by a predetermined actuation of the insertion speed, and/or of the position into which the implant is moved, and/or of the force imparted to the implant during the implantation, optionally in combination with the control of the configuration of the implant during the insertion process, e.g. a controlled change of the configuration of the implant to a predetermined final configuration. One important example of implants requiring the control of the configuration during the implantation process are synthetic implants having a first configuration, e.g. essentially linear, which during the implantation process is transformed to a curved configuration, e.g. by bending, for example influenced by the retraction of a removable stiffening device attached to or contained within the implant, or by temperature change, e.g. in the case of shape-memory materials.

Further, the present invention provides an apparatus for insertion of an implant and a system comprising said apparatus, wherein the apparatus and system are disposed to provide for control of the insertion process in response to the advancement of the insertion process, and preferably a graphic virtual representation of the insertion process.

STATE OF THE ART

U.S. Pat. No. 6,163,729 describes an insertion apparatus for introducing a flexible cochlear implant into the human cochlea, the tool essentially consisting of an elongate tube that slidably houses a pushing tube having a knob extending over the tube for manual promotion of the pushing tube. The end of the pushing tube opposite the knob can be connected to an implant for manually pushing an implant deposited in the elongate tube.

U.S. Pat. No. 7,269,461 B2 describes a cochlear implant electrode comprising electrodes embedded in a generally flexible polymer, wherein control of the bending configuration of the implant is achieved by retracting one or both of two combined stiffening elements contained in the electrode. The retraction of at least one stiffening element leads to a conformation of the electrode intermediate to the configuration adopted when both stiffening wires are retracted.

U.S. Pat. No. 6,408,855 B1 relates to a surgical method for implanting a cochlear implant, as well as to an elongate tube for sliding the implant into the cochlea. The tube may have a lengthwise slot to allow the implant to pass therethrough.

U.S. Pat. No. 5,800,500 relates to a cochlear implant electrode comprising a multitude of electric wires arranged longitudinally within a flexible insulating tubing. Preferably, the centre of the tubing is filled by a shape-memory material core that has been pretreated to transform into the shape of the scala tympani at a temperature above 35° C.

U.S. Pat. No. 5,999,859 describes a cochlear implant, which upon insertion into the cochlea is caused to adopt a conformation wrapped around the inner wall of the cochlea by retraction of a flexible element from the implant.

U.S. Pat. No. 6,374,143 B1 describes a microformed polyfluorocarbon carrier attached to electrodes and conductors that form a cochlear implant, which is said to be insertable into the cochlea without specialised insertion tools.

DE 10 2005 039455 A1 describes the measurement of the impedance between the inner wall of the cochlea and the electric contacts of a cochlear implant during the insertion for calculating the distance between the implant and the cochlea. On the basis of this impedance measurement, the insertion process is controlled. Without technical detail, the published application generally mentions the idea to control the bending of a cochlear implant in response to a signal from the impedance measurement of the distance between the implant and the cochlea.

As described in the above-mentioned publications, the insertion of cochlear implants to-date is performed by manual insertion of an implant in an originally linear elongate configuration. For the insertion, manual advancement of the implant from a guiding sheath may be used. By manual retraction of a stiffening wire, also called stylet, the configuration of the implant is changed from a first essentially elongate configuration into a second curved or spiral configuration.

For positioning the implant to the site of implantation, the implant is inserted manually through a boring adjacent to the generally spirally shaped cochlea. Due to the sensitivity of the inner cochlear surface and due to the desire to position the implant to face the sensitive nerves which are located adjacent to the inner curvature of the cochlea, which position is also referred to as close to the modiolus, a successful implantation requires the calm and experienced hand of the surgeon. In addition to the insertion of the implant by manual movement of the implant, the surgeon is at the same time required to manually retract the stylet controlling the configuration of the implant in a co-ordinated manner. A major difficulty for the implantation process is that the cochlea is hidden by sections of the skull, which only allows for a control of the advancement and bending of the implant in response to the physical impression of the insertion apparatus to the surgeon's hand. At present, no optical control of the implantation process is available.

OBJECTS OF THE INVENTION

In view of the limited control and limited reproducibility of manual implant insertion processes, the present invention aims at providing an improved apparatus for insertion of bio-compatible, e.g. bio-inert implants, and at a system comprising the apparatus, allowing the detailed control of the advancement of the implant during the insertion process in response to signals obtained for the advancement and/or force imparted onto the implant, and preferably a graphic display of the insertion process. Generally, the invention aims at providing an apparatus and a system for use in implantation, especially by minimal invasive surgery to reduce trauma to the patient.

SUMMARY OF THE INVENTION

The present invention achieves the above-mentioned objects by providing an apparatus for insertion of a rigid or a flexible implant into a body section of an implant recipient, the apparatus comprising a preferably elongate guiding section which is e.g. a section of an elongate tube having a closed circumference or a circumference including a longitudinal opening, e.g. for allowing the passage of electric wiring attached to the implant. The guiding section, which is optionally fixed to a base and/or a housing, has a longitudinal axis and an inner volume for removably receiving the implant, and for receiving an elongate first receiving member. The first receiving member at its first end is connected to a first driven actuator, preferably electrically driven, which actuator is connected to the guiding section for moving the first receiving member within the guiding section in parallel to the axis of the guiding section. The apparatus comprises a first control device for controlling the actuation of the first actuator. The first control device preferably has a human-machine interface, e.g. for input of a desired position or of a desired actuation, e.g. movement, of the first actuator relative to the guiding section. The first receiving member at its second end opposite its first end carries a gripping unit for releasably gripping a proximal end of the implant. In embodiments requiring the control of the change of configuration of the implant by actuation, the first receiving member also is connected to a driven second actuator, preferably electrically driven, for controlling the configuration of the implant, and a second control device for controlling the actuation of the second actuator. In preferred embodiments, the apparatus comprises a system for graphic display of the virtual position of an implant, preferably including the conformation of the implant, within a graphic representation of the body section receiving the implant. The virtual position and/or conformation of an implant with respect to the body section receiving the implant can be calculated on the basis of signals indicating the position of the apparatus for insertion, e.g. the position of its receiving member and/or its guiding section in combination with signals indicating the actuation of the first actuator and/or indicating the actuation of the optional second actuator.

GENERAL DESCRIPTION

In the apparatus for insertion, the actuation of the first actuator determines the advancement of the implant from the guiding section into a body section, whereas the conformation of the implant can be stable or dependent on the advancement from the guiding section, and optionally the conformation of the implant can be actuated by a second actuator.

The actuation of the second actuator can be independent from the actuation of the first actuator for arbitrary control of the conformation by actuation of the second actuator. Preferably, the actuation of the second actuator is dependent on the actuation, e.g. movement of the first actuator for a co-ordination of the change of conformation of the implant to the movement of the implant into a body section.

In embodiments comprising a second actuator, the first actuator is coupled to a first control device disposed to control its actuation, and the second actuator is coupled to a second control device to control its actuation. Preferably, the first control device of the first actuator is coupled to the second control device of the second actuator by an intermediate controller for co-ordinating the actuation of the second actuator to the actuation of the first actuator. More preferably, the first control device and the second control device are arranged in a control hierarchy, wherein the second control device is dependent on the first control device.

A second actuator for controlling the change of the implant from a first configuration to a second configuration is dispensable in embodiments of the apparatus for use in the insertion of implants having identical first and second configurations, e.g. essentially stiff implants, or for implants assuming the second configuration during implantation without additional actuation, e.g. in response to contact with the implantation site. Accordingly, embodiments of the apparatus of the invention for use with implants that do not require a treatment for controlling their conformation in coordination with the insertional movement, only contain one first actuator for movement of the implant along the guiding section, preferably with the device for display of the virtual position and/or conformation of the implant within a graphic representation of the site of implantation as well as a first control device, as described for the other embodiments of the invention.

Preferably, the first control device and/or the second control device are coupled to the force sensor or the feed rate detector for receiving signals encoding the force or feed rate of the first actuator in relation to the base, wherein the first control device is disposed to alter the control signals controlling the first and/or second actuator in response to the signals received from the force sensor and/or the feed rate detector.

Preferably, the coupling of the second actuator to the first actuator is by arrangement of the second actuator on the first actuator, resulting in the concurrent movement of the second actuator with the first actuator. In case, the second actuator is a drive, actuation of the second actuator results in a relative movement of the second actuator to the first actuator, which is independent from the movement of the first actuator. Alternatively, the coupling of the second actuator to the first actuator is by a second control device arranged for the control of the actuation of the second actuator in relation to the movement of the first actuator, e.g. in embodiments in which the second actuator is mounted on the base, e.g. parallel to the first actuator, the second control device can be disposed to move the second actuator in parallel to the first actuator in the absence of a signal for relative movement of the second actuator to the first actuator.

Preferably, the first actuator is a linear drive arranged in parallel to the axis of the guiding section, and, independent from the first actuator, the second actuator is a linear drive arranged in parallel to the axis of the guiding section. The second actuator is a conformation control device which is preferably arranged adjacent the guiding section, as the second actuator is acting on the implant for controlling the conformation of the implant in coordination with the movement of the gripping device along the guiding section. Accordingly, the second actuator is a linear drive for removal of stiffening elements for use with implants containing stiffening elements for conformation control, and/or the second actuator is a temperature control device for controlled heating or cooling of the implant arranged within the guiding section for use with implants having a temperature dependent conformation, and/or the second actuator is a pneumatic device as a pressure control device for imparting positive or negative pressure to the implant for use with implants having inflatable or deflatable sections. Further, two or more same or different second actuators can be contained in the apparatus, e.g. in addition to a second actuator being a drive, preferably a linear drive, a further second actuator which is a temperature control device or a pressure control device can be arranged at the guiding section.

In the alternative to the first actuator and the second actuator being electrically driven, they are magnetically driven or pneumatically driven. In another embodiment, the first actuator and/or the second actuator are manually driven, with the actuation of the second actuator being coupled to the actuation of the first actuator in a pre-determined relationship. In the embodiments of the invention, the actuation of the second actuator is coupled to the actuation of the first actuator, preferably in a pre-determined relationship for controlling the conformation of the implant in coordination with its movement along the guiding section and into the site of implantation. The pre-determined relationship is preferably set to control the change of the conformation of the implant from a first conformation to a second conformation in relation to its movement along the guiding section for adaptation of the conformation of the implant to the body section receiving the implant.

Further, the invention provides to a system for image guided surgery, which system comprises the apparatus as described herein for insertion of an implant, which system further comprises a position detection device for detecting the position of the apparatus for insertion relative to the body section receiving the implant. A position detection device can be provided by a stereotaxis frame which determines the positions of the apparatus for insertion and of the body section, and/or a first referencing device attached to the apparatus for insertion, the referencing device being detectable by a position detector, the system comprising a position detector for detecting the position of the first referencing device and for detecting the position of a second referencing device fixable to a body section of the implant recipient, the system comprising a computing unit receiving signals from the position detector of relative positions of the first and the second referencing devices. Preferably, the system generally comprises a computing unit receiving, storing or having access to an image of the structure of the body section receiving the implant, the computing unit being disposed to calculate the position of the implant in relation to the image of the body section, and connected to a display unit disposed to display the calculated position of the implant arranged within the image of the body section as a virtual arrangement of the implant in the image of the body section.

Preferably, the apparatus and system according to the invention are provided for use in minimal invasive surgery, because the apparatus has the advantage of allowing its insertion through a small opening in the body, e.g. a boring for passing the implant during insertion into a target position with the tip of the guiding section close to the desired site of implantation, from which tip the implant is advanced and ejected from the apparatus. Accordingly, the apparatus and system of the invention is suitable for use for insertion of an implant into a body section e.g. by a small diameter opening, e.g. a boring, especially by a boring or an opening within the tympanic membrane providing access to the cochlea. Preferably, minimal invasive surgery for cochlear implantation comprises the generation of a boring through the mastoid to provide an access opening to the cochlea (cochleastomy), avoiding damage to the tympanic membrane.

The control of the advancement of the implant, preferably in coordination with its bending into a curved second conformation, e.g. effected by actuation of a second actuator, provides for an adaptation of the conformation of the implant to the site of implantation during the insertion procedure, and hence results in a significant reduction in trauma to sensitive structures of the site of implantation, e.g. to reduced contact to the inner surface of the cochlea during insertion of an implant. Especially the system including a graphic display showing the virtual position arranged within an image of the site of the implantation, optionally in combination with an integrated display of the virtual configuration of the implant, provides for a virtual optical control of the implantation process, and therefore allows to control the apparatus for insertion in response to the current status of the insertion process, i.e. a regulated or closed-loop controlled insertion process. Preferably, the apparatus includes a display unit for displaying the virtual position of the apparatus, more preferably in combination with a display of the virtual position and conformation of the implant, integrally with a graphic representation of the body section receiving the implant. Preferably, the apparatus further is disposed for display of the virtual three-dimensional position of the guiding section, optionally including the virtual three-dimensional position of the implant. The three-dimensional position in each case preferably includes the rotational position, because this determines the direction of conformational change in relation to the axis of the implant in relation to the guiding section. This is of importance for implants which are designed to change their conformation in a non-symmetric manner, e.g. cochlear implants, wherein the conformational change into a second conformation is uni-lateral, e.g. for right-hand or left-hand mirror-symmetrical second conformation.

The invention provides an apparatus for insertion of an implant into a section of the body of an implant recipient, preferably into a body cavity, the system comprising the apparatus for insertion, disposed with a control unit for a controlled, preferably closed-loop controlled insertion process according to a predetermined movement of the implant, optionally in combination with the apparatus being disposed for performing and controlling a predetermined bending process or a reconfiguration process of the implant from an initial or first configuration to a final or second configuration, and preferably comprising a position detection device, e.g. a position detector for detecting the relative positions of a first referencing device, optionally connected to the apparatus for insertion, and at least one second referencing device, attachable to the body of the implant recipient, which position detector is connected to a computing unit disposed to display the virtual arrangement of the implant within a section of the body of the implant recipient. The virtual display of the position of the implant, preferably in combination with the display of the virtual configuration of the implant within the body section of the implant recipient, is the result of the calculated position, and optionally also the result of the virtual configuration of the implant calculated on the basis of the relative positions detected for the first referencing device and the second referencing device, and on the basis of the relative positions of the actuator within the apparatus for insertion controlling the advancement of the implant, and optionally on the basis of the actuation rate setting of the second actuator controlling the change of the configuration during the insertion process. The graphic representation of the section of the body of the implant recipient is obtained by medical imaging processes, e.g. magnetic resonance imaging (MRI), computer tomography (CT), endoscopic or external video images, ultrasound images, OCT, or X-ray exposures recorded of the site of implantation prior to the insertion of the implant, and/or during insertion of the implant.

In a further aspect, the invention provides a device for display of a virtual implant within a graphic representation of the body section receiving the implant. This embodiment can be used for planning a surgical process for implantation and is based on the calculation of the conformational change of the implant form a first conformation to a second conformation calculated on the basis of pre-determined data for the conformation of the implant in response to actuation of the first actuator and/or of the second actuator acting on the implant, e.g. on the basis of data determined for position and conformation of the implant in response to movement of the implant to the site of implantation, in combination with data of the effect of the actuation of the first actuator and/or data of the effect of the actuation of the second actuator on the conformation of the implant. Accordingly, the invention also provides for a process for planning a surgical process for implantation by use of the display of the virtual implant, including its position and conformation, within a graphic representation of the body section intended for receiving the implant.

Preferably, the advancement of the insertion process is represented by display of the virtual position and/or virtual conformation of the implant in relation to the site of implantation, which virtual position and/or virtual conformation are derived from data describing the change of conformation of the implant in response to its advancement out of the apparatus during the insertion into the body cavity. Preferably, the data describing the change of conformation of the implant in response to being subjected to actuation by the apparatus for insertion are stored in a computer and are accessible by the system of the invention, e.g. for virtual display of a conformation of the implant during the actuation by the apparatus, e.g. for virtual display used for monitoring the insertion procedure.

The display is disposed for displaying the virtual position, preferably also for displaying the virtual configuration of the implant, which virtual position and configuration, respectively, are obtained as the result of the computation, performed in a computing unit, of signals indicating the position of the first actuator controlling the advancement of the implant, and optionally of signals indicating the state of actuation of the second actuator controlling the change of configuration of the implant. Preferably, the virtual position of the implant is calculated on the basis of data of the position of the apparatus for insertion, which data are obtainable from a position detection device. A position detection device can be disposed and arranged to detect the three-dimensional position of the first actuator and/or of the second actuator and/or of the gripping means, e.g. in relation to the guiding section. As a result of a first step, the calculated position and preferably the calculated configuration of the implant in relation to the apparatus for insertion is generated. In a second step, the position and, optionally, the configuration of the implant in relation to the section of the body of the implant recipient, is calculated on the basis of the detected relative positions of the first referencing device that is connected to the apparatus for insertion, and of the second referencing device that is connected to the body of the implant recipient. In a third step, the relative position of the second referencing device in relation to an image representing the section of the body receiving the implant is determined, and in a fourth step, the data representing the virtual positioning, and optionally the virtual configuration of the implant, each in relation to the image of the body section receiving the implant are combined. Preferably, this step of combining comprises the alignment of the position, optionally also of the configuration of the implant, in relation to the image of the body section by computing the virtual position and/or virtual conformation of the implant on the basis of data defining the relative positions of the first and second referencing devices in relation to the position of the second referencing device to the image of the body section. In a fifth step, the virtual position and, preferably the virtual configuration of the implant within the image of the body section is shown for each position of the implant during the implantation process. Preferably, the virtual display of the implant, preferably also of the configuration of the implant, within an image of the body section receiving the implant, is combined with a graphic display of the force applied onto the implant by the first actuator, as the force is indicative of the resistance of the body section receiving the implant against the advancement of the implant. In addition, the apparatus can be provided with a force sensor arranged for measuring the force between the apparatus and the body section. Preferably, signals measured for forces are used for displaying the values, e.g. in relation to pre-determined maximum values, and more preferably, these signals are transmitted to control units and/or computing units controlling actuators and/or the positioning of the apparatus, for generating and transmitting the control signals to the actuators of the apparatus and/or to the positioning robot carrying the apparatus in a closed-loop control or in a feed-back control.

The image of the body section can be a two-dimensional representation, but preferably comprises data collection representing one three-dimensional image providing a three-dimensional representation of the body section, e.g. an array of sectional images or stacked images. In addition, the display screen or display device can be can be disposed for virtual three-dimensional representation of the image, e.g. for stereoscopic display.

The apparatus for insertion of an implant comprises a guiding section of a circularly closed or laterally accessible cross-section, preferably of U-shape. As an embodiment, the guiding section and the first actuator and/or the second actuator can be arranged on a base, which optionally is part of or carries a housing. Within the guiding section, a first receiving member is slidably arranged, e.g. in parallel to the axis of the guiding section. The first receiving member is connected to and actuated by a first linear actuator, which at least in a section is linearly moveable in parallel to the axis of the guiding section, and connected to the elongate first receiving member. The first actuator at least in a section is linearly moveable to impart onto the first receiving member a movement essentially parallel to the guiding section. For a linear, e.g. straight guiding section, the first receiving member is linear and the first actuator is preferably a linear actuator, whereas for a curved guiding section, the first receiving member preferably is also curved, with the first actuator designed, e.g. movable on a curved track, to move the first receiving member in a curve. The first receiving member is connected at its first end to the first actuator. For receiving an implant, the first receiving member at its second, which second end is opposite its first end, and which preferably has a gripping unit for removably attaching to a section of the implant, e.g. to the proximal end of the implant opposite the distal end of the implant heading the implant at implantation. Preferably, the implant for use with the apparatus for insertion at its proximal end has the wiring exiting the implant, which wiring contacts the electrode sections of the implant, for further connection of the wiring to a signal generation unit after positioning the implant, e.g. when the distal end of the implant is inserted to the whole extent into the body cavity of the implant recipient. The actuators can move or slide on linear or curved tracks, or the actuators can be rotary drives provided with a means for conversion of the rotary movement to a linear movement, e.g. a spindle drive, a shaft joint, a winch, or a revolving crank, optionally with an intermediate gear box each.

The guiding section is preferably of elongate shape having a U-shaped cross-section for receiving and slidably holding the implant. The elongate guiding section is advantageous for minimal invasive surgery, e.g. for introduction into a boring or another opening of small diameter.

The first receiving member which is accessing or moveably arranged within the guiding section is for holding the implant during the implantation process, e.g. for controlled actuated ejection of the implant from the guiding section through the open end thereof, which receiving member is arranged opposite the first linear actuator. In the alternative to or in addition to mechanically gripping the implant with a gripping unit provided at one end of the receiving member, the receiving member can be provided with a suction device and an opening at one end for attaching to the implant, or the receiving member can be provided with a controllable magnet for holding the implant. Accordingly, reference to a gripper or gripping section also includes any gripping means attached to the first receiving member capable of releasably holding the implant, e.g. mechanical holders, preferably a pair of clamp jaws, a suction operated holder, and/or a magnetic holder. Further, the gripping unit can hold the implant by positive fit, e.g. at the proximal end section of the implant.

Preferably, at least one, preferably two or three second actuators are arranged angled or in parallel to the first actuator for actuating, e.g. holding and moving in a controlled manner one or more stiffening elements contained in or associated with the implant, or heating or cooling and/or applying positive and/or negative pressure to the implant, for controlling the change of configuration of the implant, e.g. its bending from a linear into a curved configuration, e.g. by withdrawal of the stiffening devices or by heating in the case of shape-memory material, or inflating and/or deflating in the case of inflatable or deflatable implants.

In embodiments comprising a second actuator for controlling the configuration of the implant, the at least one second actuator is provided for actuation of the shape-changing feature of the implant. For example, if the implant can be actuated to change its configuration from a first configuration to a second one pneumatically or hydraulically, e.g. for an implant that has an inner volume that can be inflated or deflated, the second actuator can be a source of positive or negative pressure, e.g. a controlled pump. In a case in which the implant can be actuated by electric signals, e.g. if the implant has sections containing a resistance heating, the second actuator can be a controlled electric pulse generator or a controlled electric current generator. For implants changing their configuration under the influence of a magnetic field, the second actuator can be a magnetic field generator, e.g. comprising a coil for generating a magnetic field. For implants that can be actuated to change their configuration by heating, the second actuator can be a controlled heater or a magnetic field generator if the implant is designed to develop heat in response to eddy currents induced by a magnetic field. For implants that can be actuated to change their configuration by application of irradiation, e.g. light, the second actuator can be an irradiation generator, preferably an irradiation source or light source provided with a light conductor, e.g. coupled to a light conducting fibre guiding the light to sections of the implant. In one embodiment, the second actuator can be a temperature adjusting device, e.g. a heating device, which is useful for implanting implants having at least a fraction made of shape-memory compound, which upon temperature change e.g. heating, in a predetermined manner changes its configuration from a first configuration to a second configuration.

Preferably, second actuators are arranged on the first actuator for imparting only an actuation in dependence on the actuation of the first actuator, e.g. a movement relative to the first actuator, whereas no actuation of the first actuator results in no actuating, e.g. no relative movement, of the second actuator in dependence on the actuation of the first actuator, e.g. maintaining the conformation of the implant, e.g. by maintaining the relative position of the stiffening device in relation to the implant.

In the alternative, the second actuator can be mounted on the guiding section or on an optional base plate, which can e.g. carry the guiding section. The apparatus has a control unit controlling the actuation of the second actuator in relation to actuation of the first actuator. In this embodiment, in a setting where no actuation, e.g. no relative movement, of the second actuator in relation to the first actuator is desired, the second actuator, e.g. a linear actuator, is controlled for actuation, e.g. for advancement, identical to the advancement of the first actuator, whereas in a setting were relative actuation, e.g. relative movement of the second actuator to the first actuator is desired, the extent of relative actuation desired is converted by the control unit to a signal controlling the actuation of the second actuator relative to actuation of the first actuator, e.g. for movement with a difference in parallel to the first actuator, wherein the difference represents the desired relative dependence of the actuation of the second actuator from the actuation of the first actuator.

Generally, the apparatus for insertion therefore allows for a control of the relative actuation of the second actuator in relation to the movement of the first actuator, independently from the movement of the first actuator, preferably in dependence from the movement of the first actuator, especially in a pre-determined relation of the actuation of the second actuator to the actuation of the first actuator. Preferably, the pre-determined relation of the actuation of the second actuator to the movement of the first actuator comprises data acquired in advance of the insertion procedure, which data are accessible from the second control device, e.g. data of the change of conformation of the implant due to its movement out of the guiding section and into the body section, and in dependence from the actuation of the second actuator. For example, retraction of a stiffening device from an implant by actuating the second actuator in the embodiments of the invention is controlled in relation to the movement effected by the first actuator, to allow the actuation of the first actuator for advancing the implant from the guiding section with no relative movement of the second actuator, resulting in essentially no alteration of the configuration of the implant due to the ejection from the guiding section, or, alternatively, e.g. in a later phase of the implantation, in the controlled changing of the configuration of the implant by a controlled relative movement of the second actuator in dependence on the movement of the first actuator for inducing a bending of the implant during the movement from the guiding section in a predetermined manner, for co-ordination of the conformational change with the advancement of the implant from the guiding section and into the body section.

Preferably, at least the first actuator, preferably also the one or more second actuators are provided with a force sensor each, arranged to measure the force exerted onto the first receiving member by the first linear actuator, e.g. by a force sensor arranged between the first actuator and the first receiving member or arranged within or adjacent a section of the first receiving member. Especially, a force sensor is arranged to detect the force acting on the implant during the insertion process. For this purpose, a force sensor coupled to the first actuator is preferably arranged between the receiving member, e.g. its gripping unit, and the first actuator for determining the force exerted on the implant. The signal obtainable from the force sensor can be used to calculate and display the force acting onto the implant. Preferably, the force sensor is arranged adjacent the gripping section. More preferred, at least the first actuator, preferably also the second actuators are each provided with a feed rate detector arranged to measure the feed rate of the first receiving member relative to the guiding section and of the second actuator relative to the first actuator or the guiding section, respectively. In the alternative to or in addition to a feed rate sensor, a position referencing device is present on the base, and/or attached to the first actuator and/or a position referencing device attached to the second actuator.

The apparatus for insertion is preferably mounted on a positioning device, which can e.g. be positioned to the site of the implantation manually, optionally in combination with control of manual steering by observation of the visual representation of the virtual implant within the image of a body section. Preferably, the positioning device carrying the apparatus is mechanically positioned, e.g. guided in a stereotaxis frame which pre-determines the relative orientation of the body section receiving the implant to the apparatus for insertion, and provides a mechanical guidance for moving the apparatus to a pre-determined position. A preferred stereotaxis frame is specific for the anatomy of the patient, e.g. for positioning or attaching the stereotaxis frame in contact with the implant recipient, e.g. adjacent the site of implantation. Further, the apparatus can be controlled and guided by combined mechanic and electronic elements (mechatronically), e.g. mounted on a robotic positioning device, also referred to as a robot, which is manually controlled, preferably computer-controlled, most preferably in dependence from the virtual position of the implant within the image of the body section. For the purposes of this invention, the term "position" relates to the 3-dimensional orientation and distance of objects to one another, e.g. to the 3-dimensional orientation and distance of the guiding section and/or of the implant in relation to the body section receiving the implant.

Preferably, positioning of the apparatus is closed-loop controlled by back-coupling of the control signals determining the positioning of the apparatus to the position of the virtual implant within the image of the body section. Accordingly, for closed-loop control of the actuation of actuators of the apparatus for insertion and/or of the robot carrying the apparatus for insertion, a computing unit controlling the actuators of the apparatus and/or the robot can e.g. be disposed for calculation of the control signals for actuation of actuators of the apparatus and for the positioning of the robot. The control signals for the actuation of the apparatus and of the robot can e.g. be in response to differences detected by a comparison of the detected and/or calculated position of the apparatus and/or of the calculated position and/or configuration of the implant, preferably from the virtual position of the implant, to a pre-determined final position of the apparatus in respect of the site of implantation, and/or to a pre-determined virtual final position and/or virtual configuration of the implant.

The control of the actuation of the actuators of the apparatus for insertion and the control of the positioning device for positioning the apparatus can be according to a pre-determined position of the implant within a body section such that the control is set to move the apparatus over distances from a starting point to a target position adjacent the site of implantation, and to position the apparatus and the implant, respectively, from the target position to the final site of implantation. The target position, distances to the target position, and the final position of the implant can e.g. be determined prior to implantation on the basis of the structure of the body section receiving the implant, e.g. on the basis of images of the body section. In this embodiment, the control of the apparatus and of the positioning device carrying it is e.g. obtained by a control unit or a computing unit connected to the apparatus and to the positioning device carrying the apparatus, which computing unit is provided to transmit control signals to the robot, which signals control the movement of the robot, e.g. from a starting or idle position to a target position, and the computing unit is provided to transmit control signals to the actuators of the apparatus, which signals control the actuation of the actuators thereof to move the implant from the apparatus in its target position, i.e. into the site of implantation. These control signals are pre-determined by the structure of the body section receiving the implant and obtained e.g. by analysis of an image of the body section.

In the alternative to, preferably in addition to the computing unit being disposed to transmit control signals to the apparatus and the positioning device, respectively, only in accordance with a pre-determined target position of the apparatus and a site of implantation, as described in the foregoing paragraph, the computing unit is arranged to receive detector signals from at least a force sensor provided to measure the force imparted onto the implant, e.g. a force sensor attached to the first receiving member or a force sensor arranged to measure the force between the site of implantation and the implant and/or the apparatus, and is programmed to generate the control signals in response to the sensor signal, e.g. to set the control signals below maximum or above minimum values for advancement or to generate retrograde actuation signals in reaction to pre-determined force sensor signals. In this embodiment, the computing unit can be a retroactive computing unit disposed to receive signals from a force sensor of the apparatus for insertion and/or position signals from a position detector unit.

Via a data transfer line, which can be wire-bound or wireless, from the force sensor and/or the feed rate detector, and a position sensor in the alternative to or in addition to a feed rate detector, to a control device, the signals relating to the force and/or feed rate exerted onto the implant and/or signals for the position of implantation site, apparatus, first and/or second actuators, are back coupled into the control device. The control device is disposed to display the data obtained from the force sensor and/or the feed rate detector and/or the position detector, to compute the force and/or feed rate exerted onto the implant and/or the position of the implant relative to the implantation site, for display of the force and/or feed rate acting onto the implant and/or its position, and/or for reducing or augmenting the actuation of the first and/or second actuators in response to data obtained from the feed rate sensor or signals obtained from the force sensor or in response to pre-determined data, e.g. for reducing or augmenting the movement of the first actuator and/or the actuation of the second actuator to be within a pre-defined range. The control device can be disposed for direct control by data received from the force sensor and/or feed rate detector and/or data from the position detector, or can be disposed for control by or it can form a part of the computing unit, which on the basis of the data transmitted from the first and/or second actuators and of the data received from the optional position detector detecting the positions of a first referencing device attached to the apparatus for insertion, and of the second referencing device attachable to a section of the body of the implant recipient, is disposed for calculation and display of the virtual position and/or configuration of the implant. Further, the computing unit also generates data representing the virtual position and virtual configuration of the implant in relation to the body section of the implant recipient for display of the virtual position and/or configuration of the implant within the image of a body section. For an accurate representation of the position and configuration of the implant within the image of the body section, the computing unit can preferably combine the virtual display of the position and the configuration of the implant within the display of the image of the body section of the implant recipient, for producing a virtual display of the position and/or of the configuration of the implant within the image representing the body section receiving the implant.

For the calculation of data representing the virtual position and configuration of the implant and for the virtual display of the position and configuration of the implant, e.g. for visualisation of the implantation process, the computing unit is preferably disposed for determination of data representing the virtual position and configuration of the implant on the basis of signals transmitted to the actuators for their actuation, e.g. controlling the advancement of the first actuator, and on the basis of the signals controlling the actuation of a second actuator, e.g. its movement or change of temperature, pressure, irradiation and/or magnetic field, respectively. Preferably, the computing unit is disposed to calculate data representing the virtual position and virtual configuration of the implant also on the basis of the signals received from a force sensor coupled to the first actuator and/or a force sensor coupled to the second actuator, as well as on the basis of the signals received from a feed rate detector coupled to the first actuator and/or a feed rate detector coupled to the second actuator. Generally, a feed rate detector can also be referred to as a position detector comprising a data storage storing the positions assumed during movement and the time intervals in relation to these positions, which data storage can e.g. provided in a computing unit.

Preferably, the graphic display unit is disposed for display of the virtual position of the implant that is calculated from the signals received by the computing unit, preferably in combination with the virtual configuration of the implant, preferably in combination with an indication of the force exerted by the first actuator onto the implant, the force indicating the resistance of the site of the translation against the advancement of the implant. Further, the display of the virtual position, preferably in combination with the display of the virtual configuration of the implant within the image of the site of implantation is on a two-dimensional display screen, preferably representing the three-dimensional position and configuration of the implant within the image of the body section by disposition for the alternating display of views of the virtual position and of the virtual conformation of the implant within an image of a body section from different angles, e.g. a frontal, a lateral and a top view, or displaying views of the virtual position and of the virtual conformation of the implant within an image of a body section from different angles on different sections of one or more display screens.

Preferably, the image of the site of implantation has been generated previous to the implantation process by MRI or CT of the section of the body receiving the implant, e.g. by an MRI or CT image of the cochlea and of the adjacent sections of the skull, more preferably in combination with the position and orientation of the second referencing device. The image of the body section receiving the implant comprising the position and orientation of the second referencing device has the advantage of allowing the computing unit to perform a process including the steps of aligning the representation of the second referencing device contained in the image of the body section to the data determined for the position of the second referencing device as detected by the detector unit, calculating the relative position, configuration and actuation of the first referencing device, and on the basis of the geometry and dimensions of the apparatus for insertion and of the signals received by the computing unit from the apparatus for insertion, calculating data representing the virtual positioning and configuration of the implant, and of influences acting on the implant, and generating a projection or arrangement of the virtual position and virtual conformation of the implant within the image of the site of implantation.

More preferably, the virtual display of the implant within a graphic representation of a body section includes images generated during the surgical procedure, e.g. images generated by CT or X-raying.

As one embodiment of a position detection device, a position detector for detecting the referencing devices, which are also referred to as reference stars, is disposed to detect the spatial orientation and distance between the referencing devices, and hence allows the calculation of the orientation and distances of the apparatus for insertion and, accordingly, the position of its components and of the implant carried by the apparatus for insertion, and the calculation of the virtual position and virtual conformation of the implant within the body section containing the site of implantation. In general, as used herein, the term position refers to both the two-dimensional or three-dimensional position and the two-dimensional or three-dimensional orientation of an object, preferably in combination with its spacing, e.g. in relation to another object, e.g. a referencing device.

In a preferred embodiment, the apparatus for insertion is carried on the arm of a robotic positioning device, which arm is controllable by the computing unit by specific control signals determining the positioning and movement of the apparatus for insertion. The control signals can be generated on the basis of steering signals transmitted to the computing device, e.g. by manual input by an operator, e.g. a surgeon, preferably with pre-determined consideration by the computing unit of data received by the computing unit from the sensors or detectors of the apparatus for insertion. In this embodiment, a robot carrying the apparatus for insertion can be controlled by steering signals transmitting to the computing unit in respect of e.g. the desired position and desired advancement of the implant, optionally in combination with the desired configuration of the implant, while controlling the robot to actuate the apparatus for insertion in co-ordination with the signals obtained for the position, actuation and/or sensors or detector signals obtained from the apparatus for insertion. Preferably, the robot in controlled in dependence on the virtual position and virtual conformation of the implant within the graphic representation of the body section receiving the implant.

In the embodiments of the invention, the control of the first actuator and of the second actuator preferably is by a human-machine interface, which is connected to the control devices controlling the first actuator and the second actuator. The human-machine interface, for example any suitable input device having a push-button or lever or wheel for generating an electrical signal upon manipulation, can be used with the control unit being disposed to generate control signals for actuating the first actuator and/or the second actuator in a fixed relationship to the input signal received from the human-machine interface, preferably in combination with a limitation of the generation of actuating signals by preset maximum values, e.g. preset maximal values to the speed of movement of the first actuator, preset maximum values for the force detected to act onto the implant or exerted by the implant onto the body section, and, most preferably, for a preset actuation of the first actuator, to the actuation of the second actuator relative to the first actuator for co-ordinating the advancement of the implant out of the guiding section with the configuration changing from a first configuration to a second configuration, e.g. co-ordinating the advancement of the implant with bending, especially in the case of a cochlear implant. In this embodiment, the advantage of the co-ordinated actuation of the first and the second actuator is evident, as the actuation of the first actuator due to its coupling for the co-ordinated actuation of the second actuator also induces the change of configuration of the implant according to a pre-determined relationship of the advancement of the implant to its change of conformation.

The guiding section of the apparatus for insertion of a flexible implant can be temperature controlled, preferably provided with a cooling device for maintaining the temperature of the implant within the guiding section at a temperature different, e.g. lower, than the body temperature at the site of implantation. The cooling device provided at the guiding section of the apparatus is especially advantageous for use with implants comprising shape-memory materials, which upon warming acquire a different configuration, in order to defer a premature change of configuration of the implant to the change of configuration in co-ordination with the advancement of the insertion during the controlled insertion process, e.g. minimising a change of conformation while the implant is arranged within the guiding section.

DETAILED DESCRIPTION AND BEST MODE OF PRACTICING THE INVENTION

Figure 1:
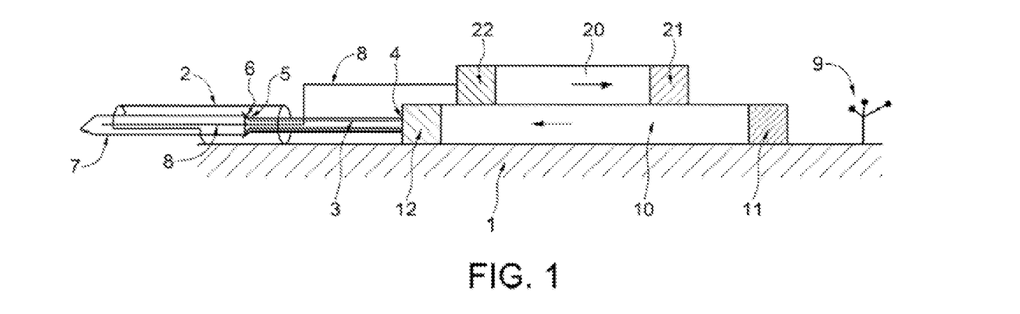
FIG. 1 shows a schematic representation of an apparatus for insertion of an implant.

As schematically shown in FIG. 1, base plate 1 carries a guiding section 2, e.g. having the general shape of an elongate tube, which guiding section 2 can have a section that is spaced from the base plate 1, which section has a lateral opening of the cross-section, e.g. a U-shaped cross-section.

A first receiving member 3 is at least partially arranged within guiding section 2, which first receiving member 3 is connected at its first end 4 to first actuator 10, which preferably is linearly moveable in the direction of the longitudinal axis of first receiving member 3. Opposite the first end 4, the second end 5 of first receiving member 3 preferably carries a gripper 6 for removably gripping the proximal end of an implant 7. Implant 7 can have one or more stiffening wires 8 arranged along its longitudinal axis and a change of the configuration of implant 7 from a first configuration, e.g. a linear configuration, to a second, e.g. curved or spiral configuration can be by withdrawal of stiffening wire 8 from the implant 7. Actuation of stiffening wire 8 is effected by moving second actuator 20 in relation to first actuator 10. Preferably, also the second actuator is a linear actuator, movable in parallel to the axis of the guiding section 2. As shown in FIG. 1, the co-ordination of relative movements of the second actuator 20 and first actuator 10 can be achieved by arranging second actuator 20 on first actuator 10.

For detecting the position of the apparatus, including its orientation in relation to a detector unit, base 1 has a first referencing device connected thereto, schematically shown as a referencing star 9 carrying at least three spheres, each terminally arranged on one of three carrier arms that are arranged in different angles around a central connection point, the carrier arms each having different lengths.

In the alternative to fixation to the base 1, the first referencing device 9 can be fixed to the first actuator 10, to the guiding section 2, or to the first receiving member 3.

The first actuator 10 has a first position detector 1 arranged for measurement of the relative position of the first actuator 10 to base 1 or to guiding section 2. Preferably, first actuator 10 further has a first force gauge or force detector 12 arranged between first actuator 10 and first receiving member 3, resulting in an effective arrangement of the force detector between the implant 8 and first actuator 10. During the implantation of the flexible implant, the position of the first actuator 10 in relation to guiding section 2 and the force between the first actuator 10 and guiding section 2 are preferably detected by a first position detector 11 and first force detector 12, respectively, for monitoring, preferably for controlling the advancement of the first actuator 10 into the direction of the guiding section 2 during the insertion process, including the monitoring, preferably controlling of the ejection of the implant 7 from guiding section 2 for insertion into the site of implantation. Generally, the force sensor or detector 12 is preferably arranged to measure the force acting on implant 7, or the force between the implant 7 and the site of implantation.

In the preferred embodiment, the apparatus has a second actuator 20 for removing a stiffening wire 8 from the implant 7 by relative movement of the second actuator 20 in relation to the first actuator 10. In order to ensure a controlled withdrawal of the stiffening wire 8 from the implant 7, it is preferred to arrange the second actuator 20 on the first actuator 10, resulting in a coordinated advancement of implant 7 including its stiffening wire 8 when no movement of the second actuator 20 in relation to first actuator 10 is effected, whereas controlled bending of the implant 7 from a first, e.g. linear configuration to a second, e.g. curved configuration, is effected by controlling the actuation of the second actuator 20, e.g. for movement, which movement in this embodiment is always a movement relative to the first actuator 10.

In the alternative, both the first actuator 10 and second actuator 20 are each independently mounted on a base 1. As well as in embodiments where the second actuator is mounted on the first actuator, also in this embodiment a second computer control device is necessary for controlling the second actuator 20 in relation to the position of the first actuator 10.

For controlled insertion of the implant 7 into the body of an implant recipient, e.g. into the cochlea in the case of implant 7 being a cochlear implant, which assumes a curved configuration upon removal of the stiffening wire 8, guiding section 2 can be introduced into an access recess or access boring made into the body section, which access is linked to the cochlea for positioning implant 7 at the cochlea and introducing implant 7 into the cochlea by actuating first actuator 10 to move across base 1 to guiding section 2 and, as appropriate, controlling the bending of the implant 7 into the appropriate curved configuration by co-ordinated retraction of the stiffening wire 8 by controlling second actuator 20 to move relative to first actuator 10, in the depicted embodiment into a direction opposite the direction of first actuator 10, as indicated by the arrows.

It is preferred that first actuator 10 carries a first position detector 11 to detect the position of the first actuator 10 relative to guiding section 2, and transmitting the first position detector signal to a control device controlling the movement of the first actuator 10 in relation to guiding section 2. Further, it is preferred that first actuator 10 is provided with a first force detector 12 to generate a signal for the force exerted between the first actuator 10 and receiving member 3, or implant 7, respectively, generally preferable a force detector 12 between stiffening wire 8 and/or implant 7 on one side, and first actuator 10 on the other side. In an alternative arrangement, which is less preferred, the first and/or the second force sensor is arranged at the end of the first and second actor, respectively, which end is opposite of the end adjacent the gripping member and stiffening wire, respectively, e.g. for measuring the force between an actor and the base 1. The signal generated by the first force detector 12 is preferably communicated to a control device controlling the movement of the first actuator 10 and/or of the second actuator 20 as the force between first actuator 10 and guiding section 2 is indicative of the resistance of the site of the implantation against the advancement of the implant 7. Accordingly, the signal from the first force detector 12 can be used to control the first control unit controlling the movement of the first actuator 10 and second actuator 20, which is in coupling with the first actuator, not to exceed predetermined maximal force values in order to avoid damage to or destruction of the site of implantation by forces exceeding a predetermined value.

The signal obtainable from the first position detector 11 can be used to more precisely determine the position of the first actuator 10 in relation to base 1 by comparing, e.g. in the control unit or in the computing unit, the signal of the first position detector 11 with the position of the first actuator 10 derivable from the control signals transmitted to the first actuator 10 effecting its movement, e.g. its advancement towards guiding section 2 for ejecting the implant 7.

For improved control of the configuration assumed by the implant due to the actuation of the second actuator 20, it is preferred that the second actuator 20 is provided with a second position detector 21 and/or a second force detector 22 for generating signals indicative of the relative position of the second actuator 20 in relation to the first actuator 10, and of the force present between the second actuator 20 and the first actuator 10, in the direction parallel to the longitudinal axis of guiding section 2, e.g. in parallel to the longitudinal axis of the implant 7.

In a preferred embodiment, first actuator 10 and second actuator 20 are electrically driven linear drives each, which can be controlled for highly precise movements, e.g. movement in increments of 1 to 10 µm.

In order to avoid metal components in the first actuator 10 and the second actuator 20, both these actuators can be pneumatically driven actuators, preferably essentially consisting of organic polymers and/or of mineral compounds, e.g. plastics and ceramics or glass, and essentially free of metal. An advantage essentially metal-free actuators, which are e.g. pneumatically driven, is that the entire apparatus including the guiding section 2, the gripper 6 on the first receiving member 3 and the base 1 can be provided free of metal for use in imaging techniques requiring the absence of metal components, e.g. in MRT. A metal-free construction of the apparatus of the invention is preferred for usage of the imaging techniques during the implant insertion procedure.

Figure 2:
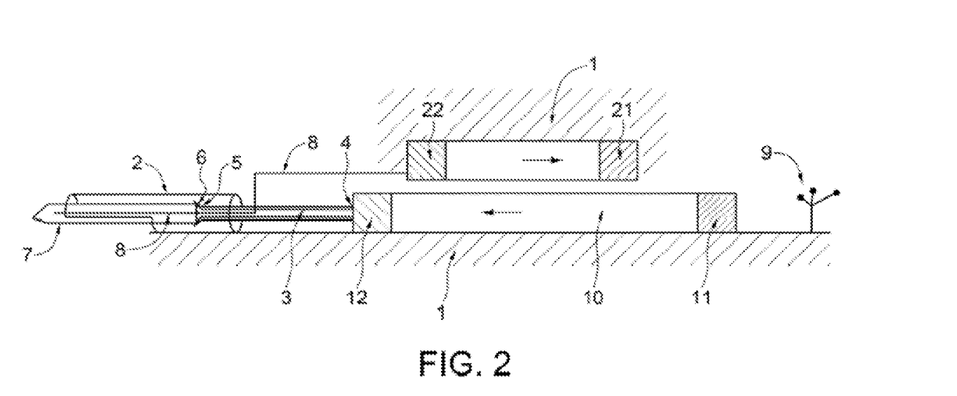
FIG. 2 shows a schematic representation of an alternative arrangement of actors of apparatus for insertion of an implant.

FIG. 2 shows an apparatus of the invention, wherein both the first actor 10 and the second actor 20 are each separately moveably mounted on base 1. In this embodiment, actuation of the second actor 20, e.g. for movement of second actuator 20 for retraction of the stiffening element 8 from the implant, is co-ordinated to the actuation of the first actuator 10, i.e. its movement towards the guiding section, by a second control device (not shown). Sensors are arranged as in the embodiment of FIG. 1.

Figure 3:
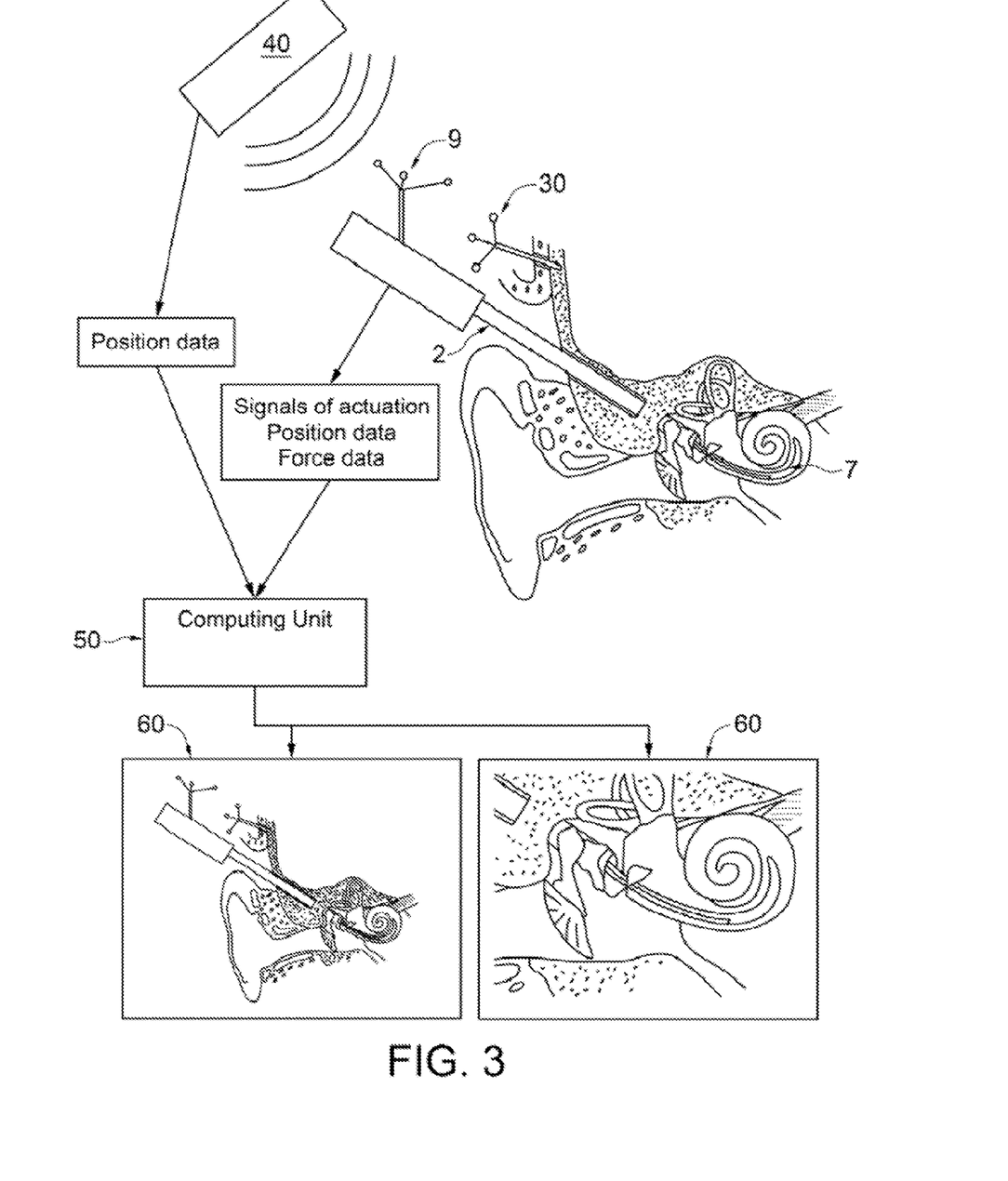
FIG. 3 shows a schematic overview of the system according to the invention comprising the apparatus for insertion of the implant, the system, including a position detector, a control device, and a display unit for display of the virtual position of the implant in a body section.

FIG. 3 shows a schematic overview of a system comprising the apparatus for insertion of an implant along with a display unit disposed to show the virtual position of the implant, which virtual position is calculated by a computing unit disposed to receive data signals from the insertion apparatus and/or from its control units controlling the movement of the first actuator and the actuation of a second actuator, and disposed to receive signals from a position detector for referencing devices, which signals are indicative of the relative position of the insertion apparatus in relation to the site of implantation. For display of the implantation site, an image representing the anatomy of the body section comprising the intended or final site of implantation and the data of the positioning of a second referencing device in the image can be accessed or is stored within the computing unit.

In detail, the computing unit 50 is disposed to relate or determine the position of the site of implantation to the position of the second referencing device 30 in order to calculate the position of the apparatus for insertion relative to the site of implantation according to position data obtainable from a position detection device, depicted here in the embodiment of a detector for detecting the relative position of first referencing device 9 to that of second referencing device 30. The detection of the relative positions of the first referencing device 9 and the second referencing device 30 is by position detector 40, which position detector 40 is arranged to transmit signals representing the relative positions of the first and second referencing devices to the computing unit 50. The computing unit 50 is disposed to align the insertion apparatus, especially its guiding section 2 relative to an image representing the body section by calculating the position of the insertion apparatus on the basis of the position of the first referencing device 9 and on the basis of the dimensions and geometry of the insertion apparatus. The position and configuration of implant 7 is calculated by computing unit 50 on the basis of the control signals transmitted to first actuator 10, second actuator 20 and, preferably, on the basis of signals obtained from first position detector 11, more preferably in combination with the signals transmitted from first force detector 12, and most preferably in combination with the signals transmitted from second position detector 21 and/or second force detector 22. The computing unit 50 can be provided to calculate the position and configuration of the implant 7 by comparing the data received for the advancement and/or position of the first actuator 10 and of the second actuator 20 with previously recorded data of the position of the implant 7 relative to guiding section 2, and hence relative to first referencing device 9 in relation to data of the actuation and/or position of the first actuator, and data previously recorded for the configuration of the implant 7 in relation to the actuation of second actuator 20 in relation to the position of first actuator 10. Accordingly, the display unit 60 shows a virtual position and virtual configuration for implant 7, calculated on the basis of signals received from the apparatus for insertion, and/or on the basis of signals indicating the actuation of the first actuator 10 and/or on the basis of the actuation of the second actuator 20, which virtual position and configuration is arranged within a previously taken image of the body section containing the site of implantation.

In this embodiment of the invention, the display unit 60 provides a virtual graphical representation of the progress of the implantation process, without requiring continuous or repeated imaging of the site of implantation during the implantation process.

Preferably, display unit 60 also provides a graphic representation of the signal obtained from the force detector 12, more preferably including a graphic representation of a predetermined maximal force value for indication of the current force imparted from first actuator 10 onto implant 7. More preferably, the display unit 60 is disposed to show the force acting onto the implant.

The invention claimed is:

1. An apparatus for insertion of a flexible implant into a body section of an implant recipient, the implant having a proximal end and a distal end, the apparatus comprising
a guiding section having a longitudinal axis and an inner volume for removably receiving the implant,
an elongate first receiving member having a first end and an opposite second end, the first end being connected to a first driven actuator which is arranged in a fixed relation to the guiding section for linear movement of the first receiving member within the guiding section in parallel to the axis of the guiding section,
wherein the first receiving member at its second end carries a gripping means for releasable attachment to the proximal end of the implant,
wherein a second actuator for controlling the conformation of the implant is coupled to the first actuator for coordination of the actuation of the second actuator to the actuation of the first actuator.

2. An apparatus according to claim 1, wherein the first actuator and the second actuator independently are electrically driven or pneumatically driven.

3. An apparatus according to claim 1, wherein the first actuator is under the control of a first control device.

4. An apparatus according to claim 3, wherein the first control device is a manual input device.

5. An apparatus according to claim 1, wherein the coupling of the second actuator to the first actuator is by a first control device arranged for control of the actuation of the first actuator, and by a second control device arranged for the control of the actuation of the second actuator in relation to the movement of the first actuator.

6. An apparatus according to claim 1, wherein the first actuator is electrically driven and is under the control of a first control unit, wherein the second actuator is electrically driven and is under the control of a second control device, and wherein for coupling of the first actuator to the second actuator for coordination the actuation of the second actuator to the actuation of the first actuator, the second control device is connected to the first control device to receive data from the first control device on the movement of the first actuator.

7. An apparatus according to claim 1, wherein the coupling of the second actuator to the first actuator is by arrangement of the second actuator on the first actuator.

8. An apparatus according to claim 1, wherein the first actuator is a linear drive arranged in parallel to the axis of the guiding section.

9. An apparatus according to claim 1, wherein the second actuator is a linear drive arranged in parallel to the axis of the guiding section.

10. An apparatus according to claim 1, wherein the second actuator is arranged at the guiding section, which second actuator is selected from a magnetic field generator, and a temperature control device for controlled heating or cooling of the implant arranged within the guiding section.

11. An apparatus according to claim 1, the apparatus comprising a force sensor disposed for measuring the force between the first receiving member and the first actuator.

12. An apparatus according to claim 1, the apparatus comprising a force sensor disposed for measuring the force exerted by the first actuator onto the implant.

13. An apparatus according to claim 1, wherein a feed rate detector is arranged between the first actuator and the base for detecting the rate of advancement of the first actuator in relation to the base.

14. An apparatus according to claim 1, wherein the coupling of the second actuator to the first actuator is by a first control device arranged for control of the actuation of the first actuator, and by a second control device arranged for the control of the actuation of the second actuator in relation to the actuation of the first actuator, the apparatus comprising a force sensor disposed for measuring force exerted by the first actuator onto the implant, which force sensor is coupled to the first control device and/or the second control device, and wherein the first control device is disposed to generate control signals controlling the first actuator and/or the second actuator in response to signals received from the force sensor.

15. An apparatus according to claim 1, wherein the coupling of the second actuator to the first actuator is by a first control device arranged for control of the actuation of the first actuator, and by a second control device arranged for the control of the actuation of the second actuator in relation to the actuation of the first actuator, the apparatus comprising a feed rate detector detecting the movement of the first actuator, which feed rate detector is coupled to the first control device and/or the second control device, and wherein the first control device is disposed to generate control signals controlling the first actuator and/or the second actuator in response to signals received from the feed rate detector.

16. An apparatus according to claim 1, comprising
a position detector disposed for detecting the relative position of the apparatus for insertion,
a computing unit disposed to receive signals indicative of the relative position of the apparatus for insertion in relation to the body section receiving the implant,
a computing unit disposed for receiving, storing or having access to an image of the structure of the body section receiving the implant,
a computing unit disposed to calculate the position of the implant in relation to the image of the body section, and connected to a display unit disposed to display the calculated position of the implant arranged within the image of the body section as a virtual arrangement of the implant in the image of the body section.

17. An apparatus according to claim 16, wherein a computing unit is disposed to receive signals from a force sensor arranged at the first receiving member.

18. An apparatus according to claim 16, wherein the apparatus is mounted on a robot for positioning the guiding section into a target position adjacent the site of implantation.

19. An apparatus according to claim 16, wherein the apparatus for insertion carries a first referencing device detectable by a position detector, wherein a second referencing device fixable to a body section of the implant recipient is detectable by the position detector, and wherein the computing unit or the detector unit is disposed for determination of the relative position of the first referencing device to the second referencing device.

20. An apparatus according to claim 16, wherein the signal indicative of the position of the apparatus for insertion receiving the implant is the relative position of the apparatus for insertion on a stereotaxis frame.

21. An apparatus according to claim 16, wherein the signal indicative of the position of the position of the body section is the relative position of the body section on a stereotaxis frame.

22. An apparatus according to claim 1, wherein the first control device and/or the second control device is a computing unit disposed to generate and transmit control signals to the first actuator and/or to the second actuator of the apparatus for insertion.

23. An apparatus according to claim 22, wherein the computing unit is disposed to generate the control signals transmitted to the first actuator for moving to a pre-determined target position relative to a site of implantation and/or wherein the computing unit is disposed to generate the control signals transmitted to the second actuator for induction of a change of the configuration of the implant according to a pre-determined sequence.

24. An apparatus according to claim 22, wherein the computing unit is disposed to generate the control signals transmitted to the first actuator dependent on signals received from the force sensor attached to the first receiving member.

25. An apparatus according to claim 1, wherein a computing unit is disposed to generate and transmit control signals to a robot carrying the apparatus for insertion for positioning the apparatus for insertion in a target position adjacent the site of implantation.

* * * * *

UNITED STATES PATENT AND TRADEMARK OFFICE
CERTIFICATE OF CORRECTION

PATENT NO. : 8,010,210 B2  
APPLICATION NO. : 12/244275  
DATED : August 30, 2011  
INVENTOR(S) : Thomas Stephan Rau et al.

It is certified that error appears in the above-identified patent and that said Letters Patent is hereby corrected as shown below:

In the Specification:

| | |
|---|---|
| Col. 4, line 17 | After "case" delete the ",". |
| Col. 6, line 52 | Delete "form" and insert --from-- therefor. |
| Col. 8, line 8 | After "can be" and before "disposed" delete "can be". |
| Col. 9, line 64 | After "setting" delete "were" and insert --where-- therefor. |
| Col. 13, line 10 | After "can e.g." insert --be--. |
| Col. 14, line 25 | After "robot" delete "in" and insert --is-- therefor. |
| Col. 15, line 55 | After "detector" delete "1" and insert --11-- therefor. |
| Col. 20, line 41 | After "of the position" and before "of the body" delete "of the position". |

Signed and Sealed this  
Twenty-ninth Day of November, 2011

David J. Kappos  
*Director of the United States Patent and Trademark Office*